US006764826B2

(12) United States Patent
Yeh et al.

(10) Patent No.: US 6,764,826 B2
(45) Date of Patent: Jul. 20, 2004

(54) INHIBITORS OF C-REACTIVE PROTEIN INDUCED INFLAMMATION

(75) Inventors: Edward T. H. Yeh, Houston, TX (US); Vincenzo Pasceri, Rome (IT); James T. Willerson, Houston, TX (US)

(73) Assignee: Board of Regents, The University of Texas System, Austin, TX (US)

( * ) Notice: Subject to any disclaimer, the term of this patent is extended or adjusted under 35 U.S.C. 154(b) by 0 days.

(21) Appl. No.: 09/878,124

(22) Filed: Jun. 8, 2001

(65) Prior Publication Data

US 2002/0142283 A1 Oct. 3, 2002

Related U.S. Application Data

(60) Provisional application No. 60/210,415, filed on Jun. 8, 2000.

(51) Int. Cl.[7] ...................... G01N 33/53; G01N 33/567; C12N 5/06; C07K 14/705

(52) U.S. Cl. ................ 435/7.1; 435/7.21; 435/337.392; 530/363

(58) Field of Search ................................ 435/7.1, 7.21, 435/173.4, 337, 342; 530/363, 399

(56) References Cited

U.S. PATENT DOCUMENTS

| | | |
|---|---|---|
| 5,220,007 A | 6/1993 | Pederson et al. |
| 5,221,605 A | 6/1993 | Bard et al. |
| 5,238,808 A | 8/1993 | Bard et al. |
| 5,284,760 A | 2/1994 | Feinstone et al. |
| 5,366,878 A | 11/1994 | Pederson et al. |
| 5,380,721 A | 1/1995 | Johnson et al. |
| 5,389,514 A | 2/1995 | Taylor |
| 5,500,345 A | 3/1996 | Soe et al. |
| 5,527,695 A | 6/1996 | Hodges et al. |
| 5,635,377 A | 6/1997 | Pederson et al. |
| 5,658,772 A | 8/1997 | Odell et al. |
| 5,789,166 A | 8/1998 | Bauer et al. |
| 5,798,208 A | 8/1998 | Crea |
| 5,830,650 A | 11/1998 | Crea |
| 6,455,046 B1 * | 9/2002 | Potempa et al. |

FOREIGN PATENT DOCUMENTS

| | | |
|---|---|---|
| WO | WO 95/31722 | 11/1995 |
| WO | WO 98/10293 | 3/1998 |

OTHER PUBLICATIONS

Tseng J et al. Binding of Human C–reactive protein (CRP) to plasma fibroneti occurs via the phosphorylcholine–binding site. Mol Immunol. 25(8):679–686, 1988.*

Lagrand WK et al. Role for complement as an intermediate between C–reactive protein and intercellular adhesion molecule–1 expression? Circulation. 104(9):E46, 2001.*

Burgess et al Possible dissociation of the heparin–binding and mitogenic activities of heparin–binding growth factor–1 from its receptor–binding activities by site–directed mutagenesis of a single lysine residue. J Cell Biol. 111:2129–2138, 1990.*

Bowie Ju, et al Deciphering the message in protein sequences: tolerance to amino acid substitutions. Science. 247(4948):1306–1310, 1990.*

Lazar E et al., Transforming growth factor alpha: mutation of aspartic acid 47 and leucine 48 results in different biological activities. Mol Cell Biol. 8:1247–1252, 1988.*

Marx et al. Enhancement of monocyte procoagulant activity by adhesion on vascular smooth muscle cells and intercellular adhesion molecule–1–transfected Chinese hamster ovary cells. Circulation. 98(9):906–11, 1998.*

Loyer et al., "Interleukin 4 inhibits the production of some acute–phase proteins by human hepatocytes in primary cultures," *FEBS Letters*, 336(2):215–220, 1993, Abstract.

Pudil et al., "Cytokines and adhesion molecules in the course of acute myocardial infarction," *Clinca Chimica Acta*, 280:127–134, 1999.

Bharadwaj et al., "The Major Receptor for C–Reactive Protein on Leukocytes Is Fcγ Receptor II," *J Exp Med*; 190(4):585–590, 1999.

Biasucci et al., "Elevated Levels of C–Reactive Protein at Discharge in Patients With Unstable Angina Predict Recurrent Instability," *Circulation*; 99(7):855–860, 1999.

Cermak et al., "C–Reactive Protein Induces Human Peripheral Blood Monocytes to Synthesize Tissue Factor," *Blood*; 82(2):513–520, 1993.

Ferreiros et al., "Independent Prognostic Value of Elevated C–Reactive Protein in Unstable Angina," *Circulation*; 100:1958–1963, 1999.

Haraldsen et al., "Cytokine–Regulated Expression of E–Selectin, Intercellular Adhesion Molecule–1 (ICAM–1), and Vascular Cell Adhesion Molecule–1 (VCAM–1) in Human Intestinal Microvascular Endothelial Cells," *J Immunol*; 156:2558–2565, 1996.

Haverkate et al., "Production of C–Reactive Protein and Risk of Coronary Events in Stable and Unstable Angina," *Lancet*; 349:462–466, 1997.

Kilpatrick and Volanakis, "Molecular Genetics, Structure, and Function of C–Reactive Protein," *Immunol Res*; 10:43–53, 1991.

(List continued on next page.)

Primary Examiner—Christina Chan
Assistant Examiner—Maher Haddad
(74) Attorney, Agent, or Firm—Fulbright & Jaworski L.L.P.

(57) ABSTRACT

The present invention relates to methods and compositions for use in treating cardiovascular disease and other inflammatory disorders that are augmented by C-reactive protein. More particularly, the invention relates to methods for screening for modulators that inhibit C-reactive protein and the use of these modulators to inhibit C-reactive protein induced vascular inflammation.

6 Claims, 7 Drawing Sheets

OTHER PUBLICATIONS

Koenig et al., "C–Reactive Protein, a Sensitive Marker of Inflammation, Predicts Future Risk of Coronary Heart Disease in Initially Healthy Middle–Aged Men," *Circulation*; 99:937–42, 1999.

Lagrand et al., "C–Reactive Protein as a Cardiovascular Risk Factor More Than an Epiphenomenon?" *Circulation*; 100:96–102, 1999.

Liuzzo et al., "The Prognostic Value of C–Reactive Protein and Serum Amyloid A Protein in Severe Unstable Angina," *N Engl J Med*; 331:417–424, 1994.

Marnell et al., "C–Reactive Protein Binds to FcγRI in Transfected COS Cells," *J Immunol*; 155:2185–2193, 1995.

Maseri, "Inflammation, Atherosclerosis, and Ischemic Events—Exploring the Hidden Side of the Moon," *N Engl J Med*; 336:1014–1016, 1997.

Pasceri and Yeh, "A Tale of Two Diseases–Atherosclerosis and Rheumatoid Arthritis," *Circulation*; 100:2124–2126, 1999.

Pasceri et al., "Modulation of C–Reactive Protein—Mediated Moncyte Chemoattractant Protein–1 Induction in Human Endothelial Cells by Anti–Atherosclerosis Drugs," *Circulation*, 103:2531–2534, 2001.

Pasceri et al., "Modulation of Vascular Inflammation In Vitro and In Vivo by Peroxisome Proliferator—Activated Receptor–γ Activators," *Circulation*; 101:235–238, 2000.

Reynolds and Vance, "C–Reactive Protein Immunohistochemical Localization in Normal and Atherosclerotic Huma Aortas," *Arch Pathol Lab Med*; 111:265–269, 1987.

Ridker et al., "C–Reactive Protein and Other Markers of Inflammation in the Prediction of Cardiovascular Disease in Women," *N. Engl J Med*; 342:836–843, 2000.

Ridker et al., "Inflammation, Aspirin, anf the Risk of Cardiovascular Disease in Apparently Healthy Men," [published erratum appears in *N Engl J Med* Jul 31;337(5):356, 1997]. *N Engl J Med*; 336:973–979, 1997.

Shah, "Circulating Makers of Inflammation for Vascular Risk Prediction—Are They Ready for Prime Time?" *Circulation*; 101:1758–1759, 2000.

Torzewski et al., "C–Reactive Protein Frequently Colocalizes With the Terminal Complement Complex in the Intima of Early Atherosclerotic Lesions of Human Coronary Arteries," *Arterioscler Thromb Vasc Biol*; 18:1386–1392, 1998.

* cited by examiner

ICAM-1

VCAM-1

E-Selectin

INHIBITORS OF C-REACTIVE PROTEIN INDUCED INFLAMMATION

This application claims priority to U.S. Provisional Application 60/210,415, which was filed on Jun. 8, 2000.

BACKGROUND OF THE INVENTION

1. Field of the Invention

The present invention relates generally to methods and compositions that modulate C-reactive protein. Such modulators are useful for inhibiting C-reactive protein induced vascular inflammation and other inflammatory diseases.

2. Description of Related Art

Inflammatory response plays an important role in the onset, development and evolution of atherosclerotic lesions. Elevated serum levels of C-reactive protein (CRP) are non-specific but sensitive markers of the acute inflammatory response. A number of epidemiological studies have shown that the acute-phase reactant C-reactive protein is an important risk factor for atherosclerosis and ischemic heart disease. Higher levels of C-reactive protein are also related to increased risk of coronary events in patients with stable and unstable angina (Liuzzo et al., 1994). The basic mechanisms of this association are not clear and C-reactive protein can merely be a marker of inflammation, with no specific role in the pathogenesis of atherosclerosis. However, although C-reactive protein is present in atherosclerotic lesions, no previous study has specifically assessed the possible effects of C-reactive protein on vascular cells.

High levels of C-reactive protein are frequently observed in patients with unstable angina and acute myocardial infarction (Liuzzo et al., 1994). Patients with unstable angina levels >3 µg/mL were associated with increased risk of coronary events (death, myocardial infarct and urgent coronary revascularization) and the association is even stronger for patients with >10 µg/mL (Liuzzo et al., 1994). This observation has suggested that C-reactive protein is a risk factor for atherosclerosis and ischemic heart disease. These studies have shown that even small increases in the levels of C-reactive protein are associated with higher risk of atherosclerosis and ischemic heart disease in apparently healthy subjects (Ridker et al., 1997; Koeing et al., 1999p; Ridker et al., 2000) and the increased risk is independent of lipid-related and non-lipid-related cardiovascular risk. In patients with stable angina, levels of C-reactive protein >3.6 µg/mL were associated with a two-fold increase in the risk of coronary events (Haverkate, et al., 1997).

C-reactive protein is an acute phase reactant protein usually present in human serum with a concentration of <1 µg/mL. However, C-reactive protein levels can increase up to 100 or even 500 times during acute inflammation. This staggering response is mainly regulated by proinflammatory cytokines, in particular interleukin-6, and is largely unaffected by anti-inflammatory drugs and hormones (Kilpatrick et al., 1991). Indeed, in patients with unstable angina with high C-reactive protein levels at discharge, C-reactive protein remains elevated during the follow-up and is associated with high risk of new coronary events, in particular in patients in the upper tertile of C-reactive protein levels (>8.6 µg/mL) (Biasucci et al., 1999). In a recent large prospective study, patients with unstable angina and C-reactive protein levels of >15 µg/mL at discharge had a 3-fold higher risk of coronary events during a 90-day follow-up (Ferreiros et al., 1999). These results suggest that the proinflammatory effects of C-reactive protein may contribute to the adverse outcome associated with higher levels of this acute phase reactant protein.

Although there is now strong evidence that C-reactive protein is an independent risk factor for ischemic heart disease (Shah 2000; Ridker et al., 2000), the mechanisms underlying this association are not clear. Since inflammatory responses play an important role in the development and evolution of atherosclerosis and may contribute to its thrombotic complications, C-reactive protein may merely be a marker of inflammatory response. Alternatively, C-reactive protein may have a direct role in the pathogenesis of atherosclerosis (Shah 2000; Lagrand et al., 1999). Due to its ligand binding properties, C-reactive protein plays a part in the innate immunity (opsonization) and in the removal of membrane and nuclear material from necrotic cells. C-reactive protein can also bind to complement factor C1q and factor H and activate the classic pathway of complement activation. In addition, recent studies have shown that C-reactive protein can bind to receptor FCγRI (with low affinity) and FCγRII (with high affinity) on leukocytes (Bharadwaj et al., 1999). Interestingly, C-reactive protein is present in atherosclerotic plaques but not in the normal vessel wall (Reynolds et al., 1987) where often colocalize with the terminal complement complex (Torzewski et al., 1998). C-reactive protein can also induce tissue factor expression by human monocytes (Cermak et al., 1993).

SUMMARY OF THE INVENTION

This invention relates generally to methods of screening for modulators of C-reactive protein (CRP). In certain embodiments of the invention, a composition of the modulator may be useful for inhibiting the development of C-reactive protein induced inflammatory diseases, e.g., cardiovascular diseases. The present inventors envision that blocking or lowering C-reactive protein levels may have beneficial effects on the evolution of atherosclerosis and may reduce the risk of coronary events.

In a specific embodiment of the present invention, it is provided a method of screening for modulators of C-reactive protein comprising: obtaining a C-reactive protein; contacting the C-reactive protein with at least a first candidate substance; and assaying for an interaction between the C-reactive protein and the first candidate substance with an assay. The assay may be used to assay for C-reactive protein induction of the expression of an adhesion molecule, a receptor, a signaling molecule, a cytokine or an enzyme. Exemplary adhesion molecules include, but are not limited to, intracellular adhesion molecule-1 (ICAM-1), vascular cell adhesion molecule-1 (VCAM), or E-selectin. A specific example of a cytokine that is contemplated in the present invention is a chemokine, e.g., monocyte chemoattractant protein-1 (MCP-1). It is known that chemokines are small cytokines that are involved in the migration and activation of cells, especially phagocytic cells and lymphocytes. Furthermore, the candidate substance may inhibit or enhance the C-reactive protein induced expression of the adhesion molecule. It can be appreciated that the modulator can modulate either C-reactive protein or a co-factor involved in the function of C-reactive protein. Further, co-factors may be isolated from serum.

In yet another embodiment, the assay endpoint comprises assaying for inducible nitric oxide synthase (iNOS) induction, receptor for advanced glycation endproducts, monocyte chemoattractant protein-1, P-selectin, endothelin-1, endothelin-receptor, interleukin-6 or heme oxygenase-1. One skilled in the art will recognize that a variety of assays may be used to assay these endpoints, such as, FACS, ELISA, Northern blotting and/or Western blotting.

In another specific embodiment, C-reactive protein can be obtained by expressing C-reactive protein in a transgenic cell or an animal; isolating the expressed C-reactive protein; procuring from serum (i.e., human serum); and procuring from cells. Further, the (a transgenic cell) cell comprises a recombinant nucleic acid sequence encoding a C-reactive protein, thus the C-reactive protein is expressed from the recombinant nucleic acid sequence.

A specific embodiment may include contacting the C-reactive protein with a first candidate substance by incubating a cell in a composition comprising C-reactive protein. One particular aspect includes that the C-reactive protein is expressed in the cell before contacting the C-reactive protein with a first candidate substance. Further, the cell is incubated with C-reactive protein and serum. The serum may be human serum. A skilled artisan will recognize that serums from other species may be utilized in the present invention, such as, bovine or guinea pig. The cell may be a human cell, such as a human umbilical vein endothelial cell. It is within the scope of the present invention that other cells may be used.

In a further embodiment, the cell may be comprised in an animal. The animal may be a mammal, such as, a human. Other exemplary mammals that can be used in the present invention, include, but are not limited to, mice, rats, dogs, cats, guinea pigs, rabbits and monkeys.

In another embodiment, the C-reactive protein or the first candidate substance may be injected into the animal. The first candidate substance may be comprised in serum, such as human or naturally occurring serum.

In yet another embodiment, the first candidate substance may be admixed with serum prior to contacting the C-reactive protein with the first candidate substance.

In a specific embodiment, the identity of the first candidate substance may be known prior to performance of the screening method. The first candidate substance may be comprised in a mixture of possible candidate substances.

In a further embodiment, the identity of the first candidate substance may be unknown prior to performance of the screening method. The identity and characteristics of the first candidate substance may be determined after the performance of the screening method. For example, the first candidate substance may be isolated after the performance of the screening method. Exemplary isolation procedures include, but are not limited to, gel-filtration chromatography, ion-exchange chromatography, immunoaffinity chromatography, hydrophobic chromatography, or aqueous-phase hydrophobic-interaction chromatography. Further, one skilled in the art would be able to utilize well-known methods to determine characteristics of a protein, i.e., electrophoresis, spectrophotometric analysis, or amino acid analysis. Furthermore, a skilled artisan will realize that the above procedures are not all inclusive, and one skilled in the art will be capable of modifying the above procedures or utilizing other well-known protein analysis procedures. Thus, it is well within the knowledge of a skilled artisan to optimize the procedures depending upon the nature of the protein, i.e., soluble protein, membrane associated protein or an insoluble protein.

In another embodiment of the present invention, also provided is a method of inhibiting C-reactive protein modulated inflammation comprising: obtaining a modulator of C-reactive protein identified by a method comprising: obtaining a C-reactive protein; contacting the C-reactive protein with at least a first candidate substance; assaying for an interaction between the C-reactive protein and the first candidate substance with an assay; incorporating the modulator of C-reactive protein in a pharmaceutically acceptable carrier to form a pharmaceutical composition; and administrating the pharmaceutical composition to a subject. The modulator may inhibit C-reactive protein induced inflammation. Further, the modulator may inhibit the development of cardiovascular complications. For example, the modulator may be given to subject with angina or myocardial infarction. Also, the modulator may be given to subject who is at risk of atherosclerosis or ischemic heart disease. In addition, the modulator inhibits the development of a stroke or other C-reactive protein induced inflammatory diseases e.g., rheumatoid arthritis, lupus and inflammatory bowel disease. The modulator may be given to the subject in a prophylactic manner. The modulator may be given in a single dose or a series of doses. Furthermore, the series of doses can be administered daily. One skilled in the art will realize that a either a variety of combinations can be utilized to administer the modulator to a patient. For example, a daily single dose may be administered or a series of doses may be administered several times throughout the day. The present invention is not construed to be limited to the specific times or doses that are specified. A skilled artisan will recognize that the times and doses may need to be altered depending upon the modulator and its characteristics or the pharmaceutical carrier characteristics that are best utilized for a given modulator.

In yet another embodiment, also provided is a modulator of C-reactive protein produced by a method comprising: obtaining a C-reactive protein; contacting the C-reactive protein with a candidate substance; assaying for an interaction between the C-reactive protein and the candidate substance; determining that the candidate substance is a modulator of C-reactive protein. The modulator may be comprised in a pharmaceutically acceptable carrier.

In still another embodiment, a C-reactive protein may be labeled prior to contacting the C-reactive protein with a first candidate substance. The labeled C-reactive protein may be utilized as a screening tool for a first candidate substance or a modulator.

In another embodiment, also provided is a method of screening for a modified modulator, wherein a first candidate substance is isolated comprising: obtaining a C-reactive protein; contacting the C-reactive protein with the first candidate substance; assaying for an interaction between the C-reactive protein and the first candidate substance to establish a baseline of a non-modified modulator; modifying the first candidate substance; contacting C-reactive protein with the modified first candidate substance; assaying for an interaction between the modified modulator in the presence of C-reactive protein and comparing the modified modulator interaction with the established baseline of the non-modified modulator. Modifying the first candidate substance comprises modification of the amino acid or nucleic acid sequence of the first candidate substance, such as, adhesion molecules, receptors, signaling molecules, cytokines, or enzymes. Exemplary modifications to the amino acid sequence include, but are not limited to, chemical mutagenesis, radiation mutagenesis, truncation of amino acids or point mutation of amino acids. In addition to chemical modifications, a skilled artisan will recognize that the modulator may be sensitive to temperature fluctuations, thus, the modulator may be modified using heat or cold. Further examples of the nucleic acid sequence of the first candidate substance comprises chemical mutagenesis, radiation mutagenesis, insertional mutagenesis, in vitro scanning mutagenesis or site-directed mutagenesis. One skilled in the art recognizes that variations of these standard, well-known modification procedures can be utilized in the present invention. Further, the modified nucleic acid sequence is inserted into an expression vector. The expression vector comprises a reporter molecule. The expression vector is transfected into cells, such as human umbilical vein endothelial cells. Further, the reporter molecule is measured for protein expression, protein activity or binding activity after transfection. One skilled in the art realizes that the reporter molecule that is used in the expression vector dictates the type of activity that is measured. Thus, the present invention can be modified to include any of the available reporter molecules known in the art. A skilled artisan recognizes that transient transfection and stable transfection can be used in the present invention. In a specific embodiment, the cells are embryonic stem cells, which after transfection are implanted into a blastocyst to produce a transgenic mouse. Furthermore, a skilled artisan is cognizant of the variety of methods to produce transgenic mice. Another example is that the modified nucleic acid sequence is injected into the embryo to produce a transgenic mouse. Thus, the present invention can be modified to develop a transgenic mouse by any of the available methods known in the art.

As used herein the specification, "a" or "an" may mean one or more. As used herein in the claim(s), when used in conjunction with the word "comprising", the words "a" or "an" may mean one or more than one. As used herein "another" may mean at least a second or more.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

FIG. 4A: Time-course of production of MCP-1 during incubation with CRP 100 $\mu$g/mL. Production of MCP-1 was expressed as time-increase in MCP-1 concentration compared with HUVEC incubated with human albumin 100 $\mu$g/mL for the same time. FIG. 4B: Time-course of production of RANTES during incubation with CRP 100 $\mu$g/mL. FIG. 4C: Dose-response of the effects of 24-hour incubation with CRP on MCP-1 production; concentration of CRP was expressed in $\mu$g/mL. NoS indicates incubation with CRP 100 $\mu$g/mL in serum-free conditions, all other experiments were performed in presence of 15% human serum.

DESCRIPTION OF ILLUSTRATIVE EMBODIMENTS

Figure 1A:
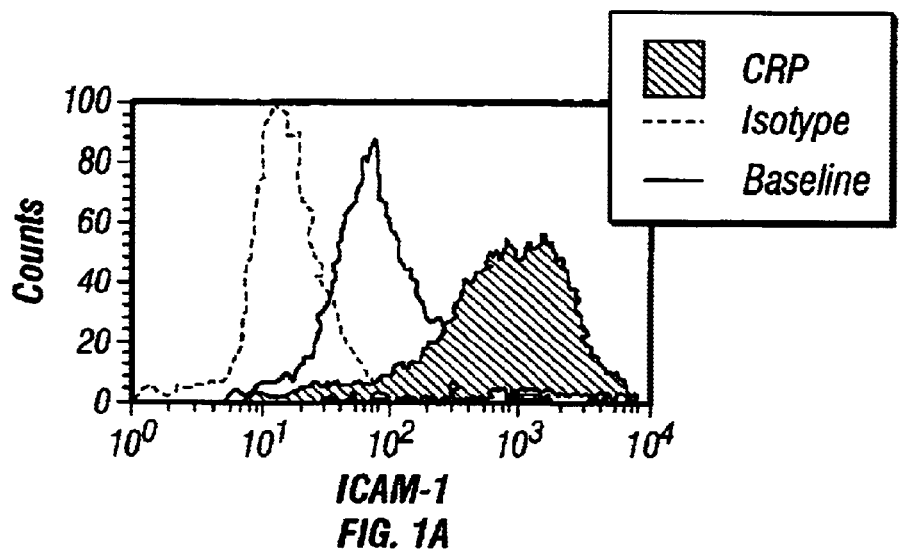
FIG. 1A, FIG. 1B, FIG. 1C, FIG. 1D, FIG. 1E and FIG. 1F: Induction of adhesion molecules expression by C-reactive protein. A large increase of ICAM-1 (FIG. 1A) and a significant increase of VCAM-1 (FIG. 1B) expression was induced by 24-hour incubation of HUVEC with 10 $\mu$g/mL of C-reactive protein. A 6-hour incubation with 10 $\mu$g/mL of C-reactive protein induced also a significant increase in E-selectin expression (FIG. 1C). Incubation with interleukin-1, 10 ng/mL for the same time-intervals resulted in induction of adhesion molecules expression similar to what observed for C-reactive protein (FIG. 1D, FIG. 1E and FIG. 1F). Experiments were performed with 15% human serum in $2^{nd}$ passage HUVEC.
Figure 1B:
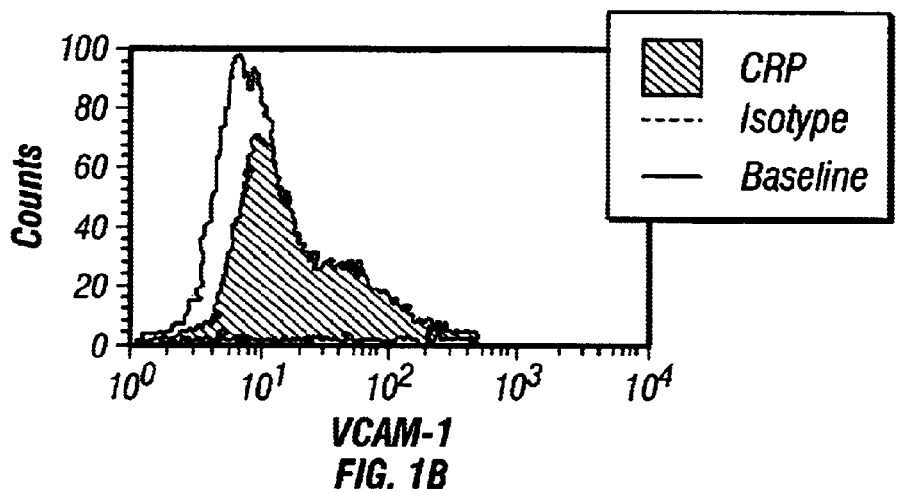
Figure 1C:
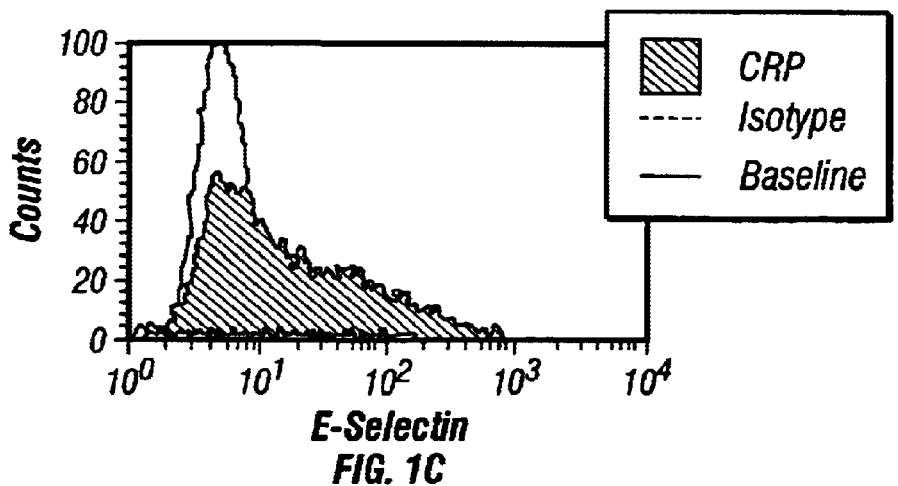
Figure 1D:
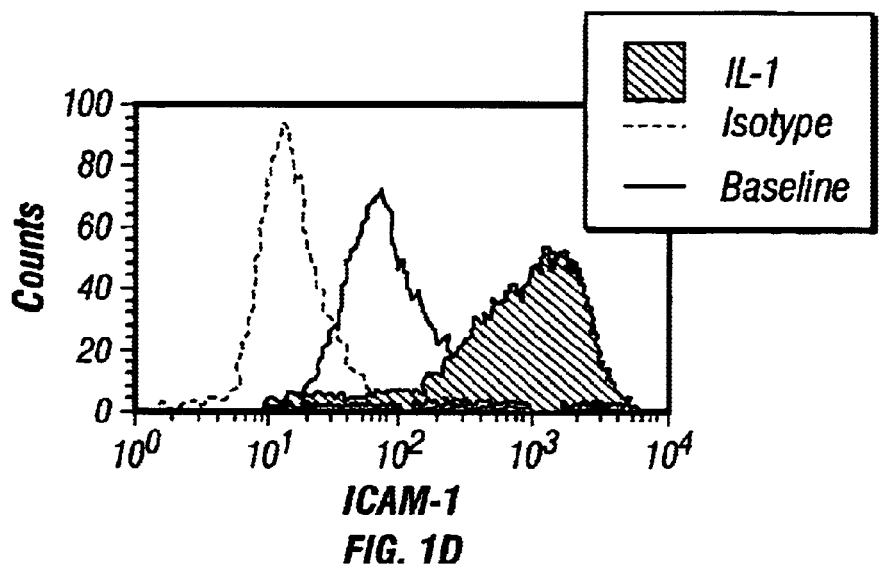
Figure 1E:
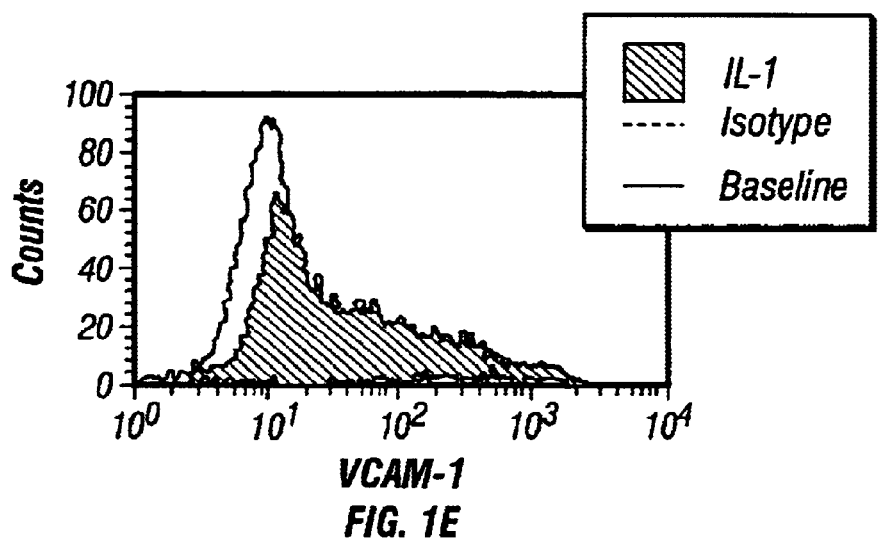
Figure 1F:
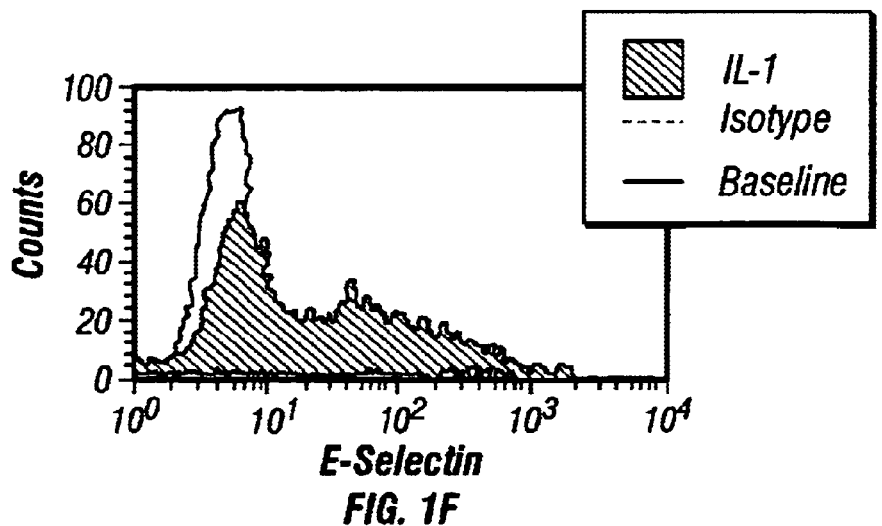
Figure 2A:
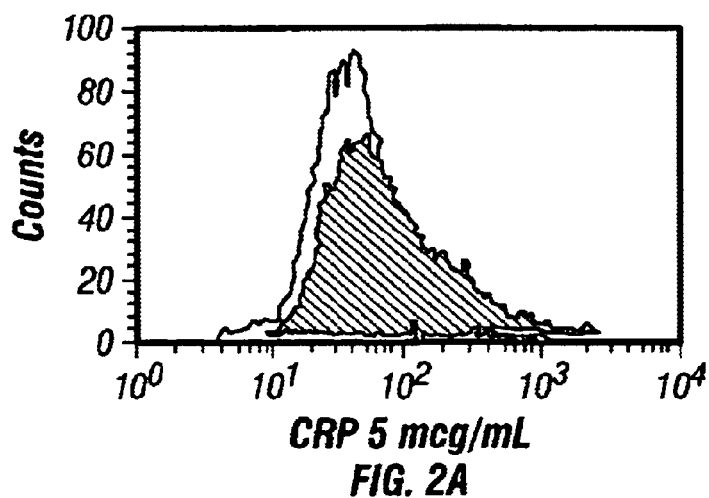
FIG. 2A, FIG. 2B, FIG. 2C, FIG. 2D, FIG. 2E and FIG. 2F: Dose response of C-reactive protein for ICAM-1 (FIG. 2A, FIG. 2B and FIG. 2C) and VCAM-1 (FIG. 2D, FIG. 2E and FIG. 2F) expression in the presence of human serum. The increase of adhesion molecules expression was already evident at 5 $\mu$g/mL (FIG. 2A and FIG. 2D) and was nearly maximum at 10 $\mu$g/mL (FIG. 2B and FIG. 2E). Further increases in C-reactive protein concentration up to 100 $\mu$g/mL (FIG. 2C and FIG. 2F) resulted in only a modest further increase in adhesion molecules expression. Experiment performed in 4th passage cells cultured with 15% human serum.
Figure 2B:
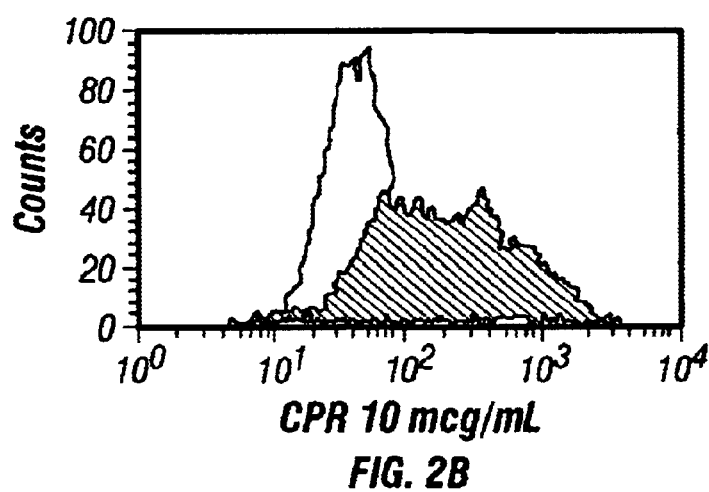
Figure 2C:
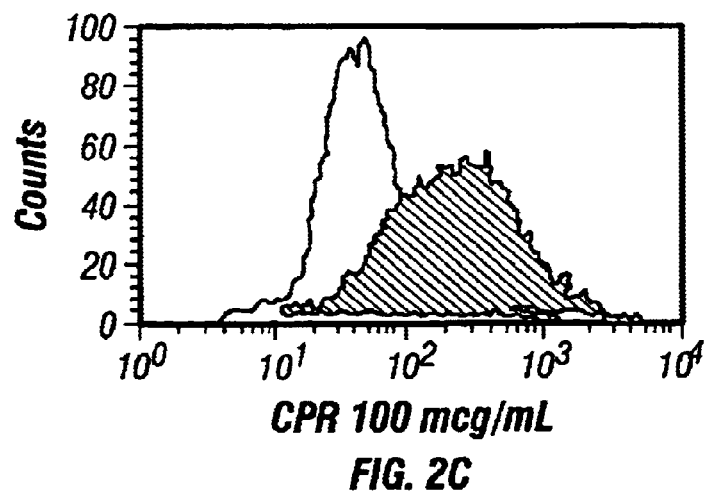
Figure 2D:
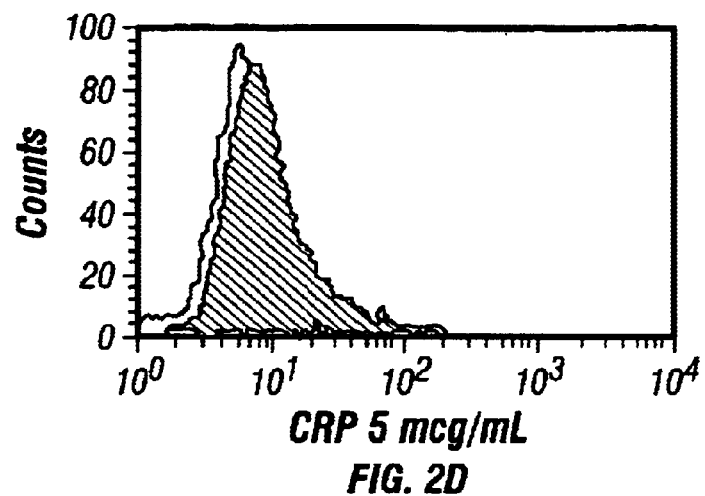
Figure 2E:
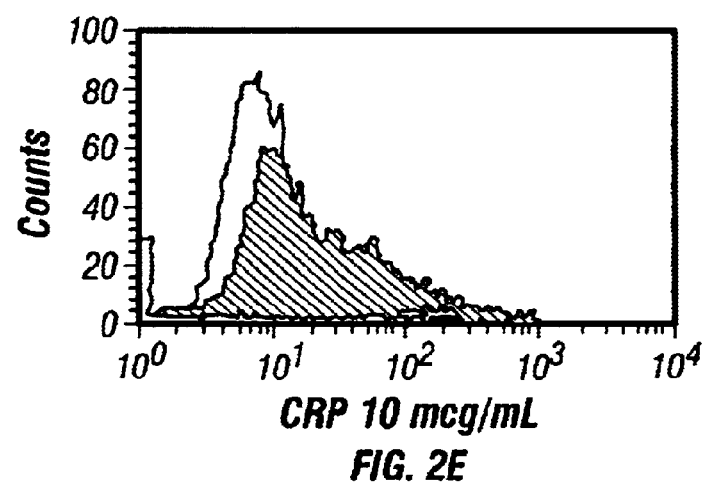
Figure 2F:
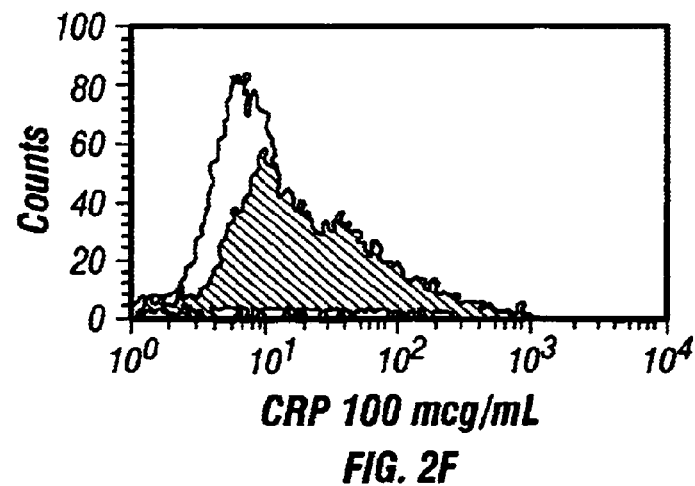

Screening For Modulators of the Protein Function

The present invention comprises methods for identifying modulators of the function of C-reactive protein. The modulator may modulate either C-reactive protein or a co-factor involved in the function of C-reactive protein. Further, co-factors may be isolated from serum. These assays may comprise random screening of large libraries of candidate substances; alternatively, the assays may be used to focus on particular classes of compounds selected with an eye towards structural attributes that are believed to make them more likely to modulate the function of C-reactive protein.

By function, it is meant that one may assay for protein expression, protein activity, or binding activity. Also, one may assay for mRNA levels, mRNA stability or mRNA degradation.

To identify a C-reactive modulator, one generally will determine the function of C-reactive protein in the presence and absence of the candidate substance. The candidate substance or modulator is defined as any substance that alters function of C-reactive protein. For example, a method generally comprises:

obtaining a C-reactive protein;

contacting the C-reactive protein with at least a first candidate substance; and assaying for an interaction between the C-reactive protein and the first candidate substance with an assay, wherein assaying comprises assaying for C-reactive protein induction of the expression of an adhesion molecule, a receptor, a signaling molecule, a cytokine or an enzyme.

Specific assay endpoints or interactions that may be measured in the present invention may include, but are not limited to assaying for inducible nitric oxide synthase (iNOS) induction, receptor for advanced glycation endproducts, monocyte chemoattractant protein-1, P-selectin, endothelin-1, endothelin-receptor, interleukin-6 or heme oxygenase-1. These assay endpoints may be assayed using standard methods such as FACS, ELISA, Northern blotting and/or Western blotting. Yet further, it is appreciated that the assays may be conducted in cell free systems, in isolated cells, or in organisms including transgenic animals.

Other screening methods may include using labeled C-reactive protein to identify a candidate substance. C-reactive protein may be labeled using standard labeling procedures that are well known and used in the art. Such labels include, but are not limited to radioactive, fluorescent, biological and enzymatic tags.

It will, of course, be understood that all the screening methods of the present invention are useful in themselves notwithstanding the fact that effective candidates may not be found. The invention provides methods for screening for such candidates, not solely methods of finding them.

1. Modulators

As used herein the term "candidate substance" refers to any molecule that may potentially inhibit or enhance C-reactive protein activity. The candidate substance may be a protein or fragment thereof, a small molecule, or even a nucleic acid molecule. It may prove to be the case that the most useful pharmacological compounds will be compounds that are structurally related to C-reactive protein or other pro-inflammatory molecules, i.e., adhesion molecules, surface receptors, cytokines, or other substances induced by C-reactive protein. Using lead compounds to help develop improved compounds is know as "rational drug design" and includes not only comparisons with know inhibitors and activators, but predictions relating to the structure of target molecules.

On the other hand, one may simply acquire, from various commercial sources, small molecule libraries that are believed to meet the basic criteria for useful drugs in an effort to "brute force" the identification of useful compounds. Screening of such libraries, including combinatorially generated libraries (e.g., peptide libraries), is a rapid and efficient way to screen large number of related (and unrelated) compounds for activity. Combinatorial approaches also lend themselves to rapid evolution of potential drugs by the creation of second, third and fourth generation compounds modeled of active, but otherwise undesirable compounds.

Candidate compounds may include fragments or parts of naturally-occurring compounds, or may be found as active combinations of known compounds, which are otherwise inactive. It is proposed that compounds isolated from natural sources, such as animals, bacteria, fungi, plant sources, including leaves and bark, and marine samples may be assayed as candidates for the presence of potentially useful pharmaceutical agents. It will be understood that the pharmaceutical agents to be screened could also be derived or synthesized from chemical compositions or man-made compounds. Thus, it is understood that the candidate substance identified by the present invention may be peptide, polypeptide, polynucleotide, small molecule inhibitors or any other compounds that may be designed through rational drug design starting from known inhibitors or stimulators.

Other suitable modulators include antisense molecules, ribozymes, and antibodies (including single chain antibodies), each of which would be specific for the target molecule. For example, an antisense molecule that bound to a translational or transcriptional start site, or splice junctions, would be ideal candidate inhibitors.

In addition to the modulating compounds initially identified, the inventors also contemplate that other sterically similar compounds may be formulated to mimic the key portions of the structure of the modulators. Such compounds, which may include peptidomimetics of peptide modulators, may be used in the same manner as the initial modulators.

An inhibitor according to the present invention may be one which exerts its inhibitory or activating effect upstream, downstream or directly on C-reactive protein. Regardless of the type of inhibitor or activator identified by the present screening methods, the effect of the inhibition or activator by such a compound results in C-reactive protein as compared to that observed in the absence of the added candidate substance.

2. In vitro Assays

A quick, inexpensive and easy assay to run is an in vitro assay. Such assays generally use isolated molecules, can be run quickly and in large numbers, thereby increasing the amount of information obtainable in a short period of time. A variety of vessels may be used to run the assays, including test tubes, plates, dishes and other surfaces such as dipsticks or beads.

One example of a cell free assay is a binding assay. While not directly addressing function, the ability of a modulator to bind to a target molecule in a specific fashion is strong evidence of a related biological effect. For example, binding of a molecule to a target may, in and of itself, be inhibitory, due to steric, allosteric or charge—charge interactions. The target may be either free in solution, fixed to a support, expressed in or on the surface of a cell. Either the target or the compound may be labeled, thereby permitting determining of binding. Usually, the target will be the labeled species, decreasing the chance that the labeling will interfere with or enhance binding. Competitive binding formats can be performed in which one of the agents is labeled, and one may measure the amount of free label versus bound label to determine the effect on binding.

A technique for high throughput screening of compounds is described in WO 84/03564. Large numbers of small peptide test compounds are synthesized on a solid substrate, such as plastic pins or some other surface. Bound polypeptide is detected by various methods.

3. In cyto Assays

The present invention also contemplates the screening of compounds for their ability to modulate C-reactive protein in cells. Various cell lines can be utilized for such screening assays, including cells specifically engineered for this purpose. For example, human umbilical vein endothelial cells (HUVEC) can be used for this assay, however, this invention should not be construed to be limited to HUVEC. Furthermore, the inventors also contemplated that transgenic cells may engineered to express C-reactive protein or a modulator of C-reactive protein or a combination of both C-reactive protein or a modulator of C-reactive protein. Furthermore, skilled artisans are cognizant that stable or transient transfections, which are well known and used in the art, may be used in the present invention.

A transgenic cell comprising an expression vector is generated by introducing into the cell the expression vector. The introduction of DNA into a cell or host cell is well known technology in the field of molecular biology and is described, for example, in Sambrook et al., (1989), Ausubel et al., (1994), and in Gerhardt et al., (1994). Methods of transfection of cells include calcium phosphate precipitation, liposome mediated transfection, DEAE dextran mediated transfection, electroporation and the like. Alternatively, cells may be simply transduced with the retrogen expression vector of the invention using ordinary technology described in the references and examples provided herein. The host cell includes a prokaryotic or eukaryotic cell, and it includes any transformable organism that is capable of replicating a vector and/or expressing a heterologous gene encoded by a vector. A host cell can, and has been, used as a recipient for vectors. Host cells may be derived from prokaryotes or eukaryotes, depending upon whether the desired result is replication of the vector or expression of part or all of the vector-encoded nucleic acid sequences. Numerous cell lines and cultures are available for use as a host cell, and they can be obtained through the American Type Culture Collection (ATCC), which is an organization that serves as an archive for living cultures and genetic materials (www.atcc.org). It is well within the knowledge and skill of a skilled artisan to determine an appropriate host. Generally this is based on the vector backbone and the desired result. A plasmid or cosmid, for example, can be introduced into a prokaryote host cell for replication of many vectors. Bacterial cells used as host cells for vector replication and/or expression include DH5α, JM109, and KC8, as well as a number of commercially available bacterial hosts such as SURE® Competent Cells and SOLOPACK™ Gold Cells (STRATAGENE®, La Jolla, Calif.). Alternatively, bacterial cells such as E. coli LE392 could be used as host cells for phage viruses. Eukaryotic cells that can be used as host cells include, but are not limited to, yeast, insects and mammals. Examples of mammalian eukaryotic host cells for replication and/or expression of a vector include, but are not limited to, HeLa, NIH3T3, Jurkat, 293, Cos, CHO, Saos, and PC12. Examples of yeast strains include, but are not limited to, YPH499, YPH500 and YPH501. Many host cells from various cell types and organisms are available and would be known to one of skill in the art. Similarly, a viral vector may be used in conjunction with either an eukaryotic or prokaryotic host cell, particularly one that is permissive for replication or expression of the vector.

Depending on the assay, culture may be required. The cell is examined using any of a number of different physiologic assays. Alternatively, molecular analysis may be performed, for example, looking at protein expression, mRNA expression (including differential display of whole cell or polyA RNA) and others.

4. In vivo Assays

In vivo assays involve the use of various animal models, including transgenic animals that have been engineered to have specific defects, or carry markers that can be used to measure the ability of a candidate substance to reach and effect different cells within the organism. Due to their size, ease of handling, and information on their physiology and genetic make-up, mice are a preferred embodiment, especially for transgenics. However, other animals are suitable as well, including rats, rabbits, hamsters, guinea pigs, gerbils, woodchucks, cats, dogs, sheep, goats, pigs, cows, horses and monkeys (including chimps, gibbons and baboons). Assays for modulators may be conducted using an animal model derived from any of these species.

In such assays, one or more candidate substances are administered to an animal, and the ability of the candidate substance(s) to alter one or more characteristics, as compared to a similar animal not treated with the candidate substance(s), identifies a modulator. The characteristics may be any of those discussed above with regard to the function of a particular compound (e.g., enzyme, receptor, hormone) or cell (e.g., growth, tumorigenicity, survival), or instead a broader indication such as angina, myocardial infarction, atherosclerosis, etc.

The present invention provides methods of screening for a candidate substance that modulates the function of C-reactive protein induced vascular inflammation. In these embodiments, the present invention is directed to a method for determining the ability of a candidate substance to modulate C-reactive protein, generally including the steps of: administering a candidate substance to the animal; and determining the ability of the candidate substance to reduce one or more characteristics of C-reactive protein.

Treatment of these animals with test compounds will involve the administration of the compound, in an appropriate form, to the animal. Administration will be by any route that could be utilized for clinical or non-clinical purposes, including but not limited to oral, nasal, buccal, or even topical. Alternatively, administration may be by intratracheal instillation, bronchial instillation, intradermal, subcutaneous, intramuscular, intraperitoneal or intravenous injection. Specifically contemplated routes are systemic intravenous injection, regional administration via blood or lymph supply, or directly to an affected site.

Determining the effectiveness of a compound in vivo may involve a variety of different criteria. Also, measuring toxicity and dose response can be performed in animals in a more meaningful fashion than in in vitro or in cyto assays.

Transgenic Animals/Knockout Animals

In one embodiment of the invention, transgenic animals are produced which contain a functional transgene encoding a functional C-reactive protein or modulator of C-reactive protein or a modified modulator of C-reactive protein. Transgenic animals expressing transgenes of C-reactive protein or a modulator or modified modulator of C-reactive, recombinant cell lines derived from such animals and transgenic embryos may be useful in methods for screening for and identifying agents that induce or repress function of C-reactive protein. Transgenic animals of the present invention also can be used as models for studying disease states.

In one embodiment of the invention, a transgene is introduced into a non-human host to produce a transgenic animal expressing a human or murine gene. The transgenic animal is produced by the integration of the transgene into the genome in a manner that permits the expression of the transgene. Methods for producing transgenic animals are generally described by Wagner and Hoppe (U.S. Pat. No. 4,873,191; which is incorporated herein by reference), Brinster et al., 1985; which is incorporated herein by reference in its entirety) and in "Manipulating the Mouse Embryo; A Laboratory Manual" 2nd edition (eds., Hogan, Beddington, Costantimi and Long, Cold Spring Harbor Laboratory Press, 1994; which is incorporated herein by reference in its entirety).

It may be desirable to replace the endogenous C-reactive protein or modulator of C-reactive protein by homologous recombination between the transgene and the endogenous gene; or the endogenous gene may be eliminated by deletion as in the preparation of "knock-out" animals. Typically, the transgene flanked by genomic sequences is transferred by microinjection into a fertilized egg. The microinjected eggs are implanted into a host female, and the progeny are screened for the expression of the transgene. Transgenic animals may be produced from the fertilized eggs from a number of animals including, but not limited to reptiles, amphibians, birds, mammals, and fish. Within a particularly preferred embodiment, transgenic mice are generated which overexpress C-reactive protein. Alternatively, the absence of C-reactive protein in "knock-out" mice permits the study of the effects that loss of C-reactive protein has on a cell in vivo. Yet further, the candidate substance may be overexpressed or "knocked-out" to further study the interaction of C-reactive protein.

As noted above, transgenic animals and cell lines derived from such animals may find use in certain testing experiments. In this regard, transgenic animals and cell lines capable of expressing C-reactive protein may be exposed to test candidate substances. These test substances can be screened for the ability to enhance or inhibit one or more characteristics of C-reactive protein, such as, expression of adhesion molecules, receptors, cytokines, signaling molecules or enzymes.

Prophylactic Uses of the C-Reactive Protein Modulators

The present invention also contemplates several prophylactic uses for modulators of C-reactive protein. Thus, it is contemplated that the modulators of the present invention may be administered to a subject in an effective amount to achieve the desired result. For example, modulators of the present invention may be administered to a subject with unstable angina or acute myocardial infarction. It is also contemplated that these compositions could decrease the biological activity typically associated with C-reactive protein induced vascular inflammation, for example, decreased atherosclerosis, decreased local inflammatory response, and decreased myocardial infarction. Yet further, the modulator may inhibit the development of a stroke or other C-reactive protein induced inflammatory diseases, e.g., rheumatoid arthritis, lupus and inflammatory bowel disease.

It is contemplated that the modulator may be administered to a subject in a single dose or a series of doses. The series of doses may be administered daily, weekly, monthly, annually, or whenever it is deemed necessary. Specifically, the modulator may be administered during or prior to an anticipated "flare-up" or "acute episode" or "exacerbation" of the disease.

Isolation of a Modulator

In specific embodiments, the candidate substance may be isolated and/or purified using standard procedures well known in the art. A candidate substance of the present invention may be a protein, a small molecule, or a nucleic acid sequence. Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. A particularly efficient method of purifying peptides is fast protein liquid chromatography or even HPLC.

Yet further, any of a wide variety of chromatographic procedures may be employed to isolate and/or purify the candidate substance or modulator that is a small molecule. For example, thin layer chromatography, gas chromatography, high performance liquid chromatography, paper chromatography, affinity chromatography or supercritical flow chromatography may be used to effect separation of various chemical species.

Partition chromatography is based on the theory that if two phases are in contact with one another, and if one or both phases constitute a solute, the solute will distribute itself between the two phases. Usually, partition chromatography employs a column, which is filled with a sorbent and a solvent. The solution containing the solute is layered on top of the column. The solvent is then passed through the column, continuously, which permits movement of the solute through the column material. The solute can then be collected based on its movement rate. The two most common types of partition chromatograph are paper chromatograph and thin-layer chromatograph (TLC); together these are called adsorption chromatography. In both cases, the matrix contains a bound liquid. Other examples of partition chromatography are gas-liquid and gel chromatography.

Paper chromatography is a variant of partition chromatography that is performed on cellulose columns in the form of a paper sheet. Cellulose contains a large amount of bound water even when extensively dried. Partitioning occurs between the bound water and the developing solvent. Frequently, the solvent used is water. Usually, very small volumes of the solution mixture to be separated is placed at top of the paper and allowed to dry. Capillarity draws the solvent through the paper, dissolves the sample, and moves the components in the direction of flow. Paper chromatograms may be developed for either ascending or descending solvent flow. Two dimensional separations are permitted by changing the axis of migration 90° after the first run.

Thin layer chromatography (TLC) is very commonly used to separate lipids and, therefore, is considered a preferred embodiment of the present invention. TLC has the advantages of paper chromatography, but allows the use of any substance that can be finely divided and formed into a uniform layer. In TLC, the stationary phase is a layer of sorbent spread uniformly over the surface of a glass or plastic plate. The plates are usually made by forming a slurry of sorbent that is poured onto the surface of the gel after creating a well by placing tape at a selected height along the perimeter of the plate. After the sorbent dries, the tape is removed and the plate is treated just as paper in paper chromatography. The sample is applied and the plate is contacted with a solvent. Once the solvent has almost reached the end of the plate, the plate is removed and dried. Spots can then be identified by fluorescence, immunologic identification, counting of radioactivity, or by spraying varying reagents onto the surface to produce a color change.

In Gas-Liquid chromatography (GLC), the mobile phase is a gas and the stationary phase is a liquid adsorbed either to the inner surface of a tube or column or to a solid support. The liquid usually is applied as a solid dissolved in a volatile solvent such as ether. The sample, which may be any sample that can be volatized, is introduced as a liquid with an inert gas, such as helium, argon or nitrogen, and then heated. This gaseous mixture passes through the tubing. The vaporized compounds continually redistribute themselves between the gaseous mobile phase and the liquid stationary phase, according to their partition coefficients.

The advantage of GLC is in the separation of small molecules. Sensitivity and speed are quite good, with speeds that approach 1000 times that of standard liquid chromatography. By using a non-destructive detector, GLC can be used preparatively to purify grams quantities of material. The principal use of GLC has been in the separation of alcohols, esters, fatty acids and amines.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related in a simple matter to molecular weight.

The gel material for gel chromatography is a three-dimensional network whose structure is usually random. The gels consist of cross-linked polymers that are generally inert, do not bind or react with the material being analyzed, and are uncharged. The space filled within the gel is filled with liquid and this liquid occupies most of the gel volume. Common gels are dextran, agarose and polyacrylamide; they are used for aqueous solution.

High Performance Liquid Chromatography (HPLC) is characterized by a very rapid separation with extraordinary resolution of peaks. This is achieved by the use of very fine particles and high pressure to maintain and adequate flow rate. Separation can be accomplished in a matter of minutes, or a most an hour. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Affinity Chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (alter pH, ionic strength, temperature, etc.).

The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand. One of the most common forms of affinity chromatography is immunoaffinity chromatography.

Mutagenesis

Where employed, mutagenesis will be accomplished by a variety of standard, mutagenic procedures. Mutation is the process whereby changes occur in the quantity or structure of an organism. Mutation can involve modification of the nucleotide sequence of a single gene, blocks of genes or whole chromosome. Changes in single genes may be the consequence of point mutations which involve the removal, addition or substitution of a single nucleotide base within a DNA sequence, or they may be the consequence of changes involving the insertion or deletion of large numbers of nucleotides.

Mutations can arise spontaneously as a result of events such as errors in the fidelity of DNA replication or the movement of transposable genetic elements (transposons) within the genome. They also are induced following exposure to chemical or physical mutagens. Such mutation-inducing agents include ionizing radiations, ultraviolet light and a diverse array of chemical such as alkylating agents and polycyclic aromatic hydrocarbons all of which are capable of interacting either directly or indirectly (generally following some metabolic biotransformations) with nucleic acids. The DNA lesions induced by such environmental agents may lead to modifications of base sequence when the affected DNA is replicated or repaired and thus to a mutation. Mutation also can be site-directed through the use of particular targeting methods.

1. Random Mutagenesis a) Insertional Mutagenesis

Insertional mutagenesis is based on the inactivation of a gene via insertion of a known DNA fragment. Because it involves the insertion of some type of DNA fragment, the mutations generated are generally loss-of-function, rather than gain-of-function mutations. However, there are several examples of insertions generating gain-of-function mutations (Oppenheimer et al., 1991). Insertion mutagenesis has been very successful in bacteria and Drosophila (Cooley et al., 1988) and recently has become a powerful tool in corn (Schmidt et al., 1987); Arabidopsis; (Marks et al., 1991; Koncz et al., 1990); and Antirrhinum (Sommer et al., 1990).

Transposable genetic elements are DNA sequences that can move (transpose) from one place to another in the genome of a cell. The first transposable elements to be recognized were the Activator/Dissociation elements of *Zea mays* (McClintock, 1957). Since then, they have been identified in a wide range of organisms, both prokaryotic and eukaryotic.

Transposable elements in the genome are characterized by being flanked by direct repeats of a short sequence of DNA that has been duplicated during transposition and is called a target site duplication. Virtually all transposable elements whatever their type, and mechanism of transposition, make such duplications at the site of their insertion. In some cases the number of bases duplicated is constant, in other cases it may vary with each transposition event. Most transposable elements have inverted repeat sequences at their termini. These terminal inverted repeats may be anything from a few bases to a few hundred bases long and in many cases they are known to be necessary for transposition.

Eukaryotic elements can be classified according to their structure and mechanism of transportation. The primary distinction is between elements that transpose via an RNA intermediate, and elements that transpose directly from DNA to DNA.

Elements that transpose via an RNA intermediate often are referred to as retrotransposons, and their most characteristic feature is that they encode polypeptides that are believed to have reverse transcriptionase activity. There are two types of retrotransposon. Some resemble the integrated proviral DNA of a retrovirus in that they have long direct repeat sequences, long terminal repeats (LTRs), at each end. The similarity between these retrotransposons and proviruses extends to their coding capacity. They contain sequences related to the gag and pol genes of a retrovirus, suggesting that they transpose by a mechanism related to a retroviral life cycle. Retrotransposons of the second type have no terminal repeats. They also code for gag- and pol-like polypeptides and transpose by reverse transcription of RNA intermediates, but do so by a mechanism that differs from that or retrovirus-like elements. Transposition by reverse transcription is a replicative process and does not require excision of an element from a donor site.

Transposable elements are an important source of spontaneous mutations, and have influenced the ways in which genes and genomes have evolved. They can inactivate genes by inserting within them, and can cause gross chromosomal rearrangements either directly, through the activity of their transposases, or indirectly, as a result of recombination between copies of an element scattered around the genome. Transposable elements that excise often do so imprecisely and may produce alleles coding for altered gene products if the number of bases added or deleted is a multiple of three.

Transposable elements themselves may evolve in unusual ways. If they were inherited like other DNA sequences, then copies of an element in one species would be more like copies in closely related species than copies in more distant species. This is not always the case, suggesting that transposable elements are occasionally transmitted horizontally from one species to another.

b) Chemical Mutagenesis

Chemical mutagenesis offers certain advantages, such as the ability to find a full range of mutant alleles with degrees of phenotypic severity, and is facile and inexpensive to perform. The majority of chemical carcinogens produce mutations in DNA. Benzo[a]pyrene, N-acetoxy-2-acetyl aminofluorene and aflotoxin B1 cause GC to TA transversions in bacteria and mammalian cells. Benzo[a]pyrene also can produce base substitutions such as AT to TA. N-nitroso compounds produce GC to AT transitions. Alkylation of the O4 position of thymine induced by exposure to n-nitrosoureas results in TA to CG transitions.

A high correlation between mutagenicity and carcinogenity is the underlying assumption behind the Ames test (McCann et al., 1975) which speedily assays for mutants in a bacterial system, together with an added rat liver homogenate, which contains the microsomal cytochrome P450, to provide the metabolic activation of the mutagens where needed.

In vertebrates, several carcinogens have been found to produce mutation in the ras proto-oncogene. N-nitroso-N-methyl urea induces mammary, prostate and other carcinomas in rats with the majority of the tumors showing a G to A transition at the second position in codon 12 of the Ha-ras oncogene. Benzo[a]pyrene-induced skin tumors contain A to T transformation in the second codon of the Ha-ras gene.

c) Radiation Mutagenesis

The integrity of biological molecules is degraded by the ionizing radiation. Adsorption of the incident energy leads to the formation of ions and free radicals, and breakage of some covalent bonds. Susceptibility to radiation damage appears quite variable between molecules, and between different crystalline forms of the same molecule. It depends on the total accumulated dose, and also on the dose rate (as once free radicals are present, the molecular damage they cause depends on their natural diffusion rate and thus upon real time). Damage is reduced and controlled by making the sample as cold as possible.

Ionizing radiation causes DNA damage and cell killing, generally proportional to the dose rate. Ionizing radiation has been postulated to induce multiple biological effects by direct interaction with DNA, or through the formation of free radical species leading to DNA damage (Hall, 1988). These effects include gene mutations, malignant transformation, and cell killing. Although ionizing radiation has been demonstrated to induce expression of certain DNA repair genes in some prokaryotic and lower eukaryotic cells, little is known about the effects of ionizing radiation on the regulation of mammalian gene expression (Borek, 1985). Several studies have described changes in the pattern of protein synthesis observed after irradiation of mammalian cells. For example, ionizing radiation treatment of human malignant melanoma cells is associated with induction of several unidentified proteins (Boothman et al., 1989). Synthesis of cyclin and co-regulated polypeptides is suppressed by ionizing radiation in rat REF52 cells, but not in oncogene-transformed REF52 cell lines (Lambert and Borek, 1988). Other studies have demonstrated that certain growth factors or cytokines may be involved in x-ray-induced DNA damage. In this regard, platelet-derived growth factor is released from endothelial cells after irradiation (Witte, et al., 1989).

In the present invention, the term "ionizing radiation" means radiation comprising particles or photons that have sufficient energy or can produce sufficient energy via nuclear interactions to produce ionization (gain or loss of electrons). An exemplary and preferred ionizing radiation is an x-radiation. The amount of ionizing radiation needed in a given cell generally depends upon the nature of that cell. Typically, an effective expression-inducing dose is less than a dose of ionizing radiation that causes cell damage or death directly. Means for determining an effective amount of radiation are well known in the art.

In a certain embodiments, an effective expression inducing amount is from about 2 to about 30 Gray (Gy) administered at a rate of from about 0.5 to about 2 Gy/minute. Even more preferably, an effective expression inducing amount of ionizing radiation is from about 5 to about 15 Gy. In other embodiments, doses of 2–9 Gy are used in single doses. An effective dose of ionizing radiation may be from 10 to 100 Gy, with 15 to 75 Gy being preferred, and 20 to 50 Gy being more preferred.

Any suitable means for delivering radiation to a tissue may be employed in the present invention in addition to external means. For example, radiation may be delivered by first providing a radiolabeled antibody that immunoreacts with an antigen of the tumor, followed by delivering an effective amount of the radiolabeled antibody to the tumor. In addition, radioisotopes may be used to deliver ionizing radiation to a tissue or cell.

d) In vitro Scanning Mutagenesis

Random mutagenesis also may be introduced using error prone PCR (Cadwell and Joyce, 1992). The rate of mutagenesis may be increased by performing PCR in multiple tubes with dilutions of templates.

One particularly useful mutagenesis technique is alanine scanning mutagenesis in which a number of residues are substituted individually with the amino acid alanine so that the effects of losing side-chain interactions can be determined, while minimizing the risk of large-scale perturbations in protein conformation (Cunningham et al., 1989).

In recent years, techniques for estimating the equilibrium constant for ligand binding using minuscule amounts of protein have been developed (Blackburn et al., 1991; U.S. Pat. Nos. 5,221,605 and 5,238,808). The ability to perform functional assays with small amounts of material can be exploited to develop highly efficient, in vitro methodologies for the saturation mutagenesis of antibodies. The inventors bypassed cloning steps by combining PCR mutagenesis with coupled in vitro transcription/translation for the high throughput generation of protein mutants. Here, the PCR products are used directly as the template for the in vitro transcription/translation of the mutant single chain antibodies. Because of the high efficiency with which all 19 amino acid substitutions can be generated and analyzed in this way, it is now possible to perform saturation mutagenesis on numerous residues of interest, a process that can be described as in vitro scanning saturation mutagenesis (Burks et al., 1997).

In vitro scanning saturation mutagenesis provides a rapid method for obtaining a large amount of structure-function information including: (i) identification of residues that modulate ligand binding specificity, (ii) a better understanding of ligand binding based on the identification of those amino acids that retain activity and those that abolish activity at a given location, (iii) an evaluation of the overall plasticity of an active site or protein subdomain, (iv) identification of amino acid substitutions that result in increased binding.

e) Random Mutagenesis by Fragmentation and Reassembly

A method for generating libraries of displayed polypeptides is described in U.S. Pat. No. 5,380,721. The method comprises obtaining polynucleotide library members, pooling and fragmenting the polynucleotides, and reforming fragments therefrom, performing PCR amplification, thereby homologously recombining the fragments to form a shuffled pool of recombined polynucleotides.

2. Site-Directed Mutagenesis

Structure-guided site-specific mutagenesis represents a powerful tool for the dissection and engineering of protein-ligand interactions (Wells 1996, Braisted et al, 1996). The technique provides for the preparation and testing of sequence variants by introducing one or more nucleotide sequence changes into a selected DNA.

Site-specific mutagenesis uses specific oligonucleotide sequences which encode the DNA sequence of the desired mutation, as well as a sufficient number of adjacent, unmodified nucleotides. In this way, a primer sequence is provided with sufficient size and complexity to form a stable duplex on both sides of the deletion junction being traversed. A primer of about 17 to 25 nucleotides in length is preferred, with about 5 to 10 residues on both sides of the junction of the sequence being altered.

The technique typically employs a bacteriophage vector that exists in both a single-stranded and double-stranded form. Vectors useful in site-directed mutagenesis include vectors such as the M13 phage. These phage vectors are commercially available and their use is generally well known to those skilled in the art. Double-stranded plasmids are also routinely employed in site-directed mutagenesis, which eliminates the step of transferring the gene of interest from a phage to a plasmid.

In general, one first obtains a single-stranded vector, or melts two strands of a double-stranded vector, which includes within its sequence a DNA sequence encoding the desired protein or genetic element. An oligonucleotide primer bearing the desired mutated sequence, synthetically prepared, is then annealed with the single-stranded DNA preparation, taking into account the degree of mismatch when selecting hybridization conditions. The hybridized product is subjected to DNA polymerizing enzymes such as *E. coli* polymerase I (Klenow fragment) in order to complete the synthesis of the mutation-bearing strand. Thus, a heteroduplex is formed, wherein one strand encodes the original non-mutated sequence, and the second strand bears the desired mutation. This heteroduplex vector is then used to transform appropriate host cells, such as *E. coli* cells, and clones are selected that include recombinant vectors bearing the mutated sequence arrangement.

Comprehensive information on the functional significance and information content of a given residue of protein can best be obtained by saturation mutagenesis in which all 19 amino acid substitutions are examined. The shortcoming of this approach is that the logistics of multiresidue saturation mutagenesis are daunting (Warren et al., 1996, Brown et al., 1996; Zeng et al., 1996; Burton and Barbas, 1994; Yelton et al., 1995; Jackson et al., 1995; Short et al., 1995; Wong et al., 1996; Hilton et al., 1996). Hundreds, and possibly even thousands, of site specific mutants must be studied. However, improved techniques make production and rapid screening of mutants much more straightforward. See also, U.S. Pat. Nos. 5,798,208 and 5,830,650, for a description of "walk-through" mutagenesis.

Other methods of site-directed mutagenesis are disclosed in U.S. Pat. Nos. 5,220,007; 5,284,760; 5,354,670; 5,366,878; 5,389,514; 5,635,377; and 5,789,166.

Rational Drug Design

The goal of rational drug design is to produce structural analogs of biologically active compounds. By creating such analogs, it is possible to fashion drugs which are more active or stable than the natural molecules, which have different susceptibility to alteration or which may affect the function of various other molecules. In one approach, one would generate three-dimensional structures for C-reactive protein and a modulator of C-reactive protein or a fragment thereof. This could be accomplished by X-ray crystallography, computer modeling or by a combination of both approaches. An alternative approach, involves the random replacement of functional groups throughout the C-reactive protein or a modulator of C-reactive protein, and the resulting affect on function determined.

It also is possible to isolate a C-reactive protein or a modulator of C-reactive protein specific antibody, selected by a functional assay, and then solve its crystal structure. In principle, this approach yields a pharmacore upon which subsequent drug design can be based. It is possible to bypass protein crystallography altogether by generating anti-idiotypic antibodies to a functional, pharmacologically active antibody. As a mirror image of a mirror image, the binding site of anti-idiotype would be expected to be an analog of the original antigen. The anti-idiotype could then be used to identify and isolate peptides from banks of chemically- or biologically-produced peptides. Selected peptides would then serve as the pharmacore. Anti-idiotypes may be generated using the methods described herein for producing antibodies, using an antibody as the antigen.

Formulations and Routes for Administration to Patients

Where clinical applications are contemplated, it will be necessary to prepare pharmaceutical compositions—expression vectors, virus stocks, proteins, antibodies and drugs—in a form appropriate for the intended application. Generally, this will entail preparing compositions that are essentially free of pyrogens, as well as other impurities that could be harmful to humans or animals.

One will generally desire to employ appropriate salts and buffers to render delivery vectors stable and allow for uptake by target cells. Buffers also will be employed when recombinant cells are introduced into a patient. Aqueous compositions of the present invention comprise an effective amount of the vector to cells, dissolved or dispersed in a pharmaceutically acceptable carrier or aqueous medium. Such compositions also are referred to as inocula. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well know in the art. Except insofar as any conventional media or agent is incompatible with the vectors or cells of the present invention, its use in therapeutic compositions is contemplated. Supplementary active ingredients also can be incorporated into the compositions.

The active compositions of the present invention may include classic pharmaceutical preparations. Administration of these compositions according to the present invention will be via any common route so long as the target tissue is available via that route. This includes oral, nasal, buccal, rectal, vaginal or topical. Alternatively, administration may be by orthotopic, intradermal, subcutaneous, intramuscular, intraperitoneal or intravenous injection. Such compositions would normally be administered as pharmaceutically acceptable compositions, described supra.

The active compounds also may be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For oral administration the compositions of the present invention may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient also may be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

Example 1

C-Reactive Protein

All experiments were performed on human umbilical vein endothelial cells (HUVEC, from Cascade Biology). HUVEC were grown in M199 medium with endothelial cell growth supplement, heparin and 15% fetal bovine serum or human serum. Cells were used at passage 2 to 4.

Recombinant human C-reactive protein and highly purified C-reactive protein from human serum were purchased from Biochem. Purity of C-reactive protein preparations was confirmed by 12% SDS-PAGE; no contaminating proteins were detected in overloaded gels. Interleukin-1 was provided by RandD systems. Human serum and fetal bovine serum were purchased from Sigma.

Example 2

Screening Protocols

Modulators of C-reactive protein are screened in vivo or in vitro using standard procedures. For example, C-reactive protein is contacted or admixed with a candidate substance and the interaction between the C-reactive protein and the candidate substance is assayed using FACS, ELISA, Northern blotting and/or Western blotting.

The interaction between the C-reactive protein and the candidate substance results in the induction of the expression of an adhesion molecule, a receptor, a signaling molecule, a cytokine or an enzyme. Specific endpoints or interactions that are measured may include assaying for inducible nitric oxide synthase (iNOS) induction, receptor for advanced glycation endproducts, monocyte chemoattractant protein-1, P-selectin, endothelin-1, endothelin-receptor, interleukin-6 or heme oxygenase-1.

Other screening methods include using labeled C-reactive protein to identify a candidate substance. C-reactive protein is labeled using standard labeling procedures. Such labels include radioactive, fluorescent, biological and enzymatic tags.

Example 3

Detection of Adhesion Molecules in the Presence of Serum

HUVEC were incubated with human C-reactive protein at the concentration indicated for 24 hours. Cells were detached by incubation with 10 mmol/L EDTA in PBS (without trypsin), washed with PBS buffer and suspended in PBS with 1% FBS and 0.1% sodium azide. Cell were then stained with R-Phycoerythrin labeled monoclonal antibodies (Pharmingen) against the adhesion molecules VCAM-1 (CD106) or ICAM-1 (CD54) or with Phycoerythrin labeled isotype IgG as control. For detection of E-selectin, HUVEC were incubated for 6 hours with C-reactive protein and then stained with a FITC labeled monoclonal antibody against E-selectin (RandD Systems) or the appropriate isotype control (Pasceri et al., 2000). R-Phycoerythrin labeled monoclonal antibodies (Pharmingen) against the C-reactive protein receptors FC$\gamma$RI and FC$\gamma$RII (Marnell et al., 1995; Bharadwaj et al., 1999) were also used.

The staining procedure was performed on ice for 30 minutes, followed by washing. The fluorescence intensity of 9000 cells for each sample was quantified by a FACS CaliburTM analyser (Becton Dickinson). All experiments were performed in triplicate.

Unstimulated HUVEC expressed low levels of ICAM-1, but no VCAM-1 and E-selectin (FIG. 1). Culture of the cells with human serum did not change baseline expression of adhesion molecules. In cells cultured with complete human serum incubation with recombinant C-reactive protein, 10 $\mu$g/mL for 24-hours, caused a large increase in ICAM-1 and VCAM-1 expression (FIG. 1). Similar results were obtained using highly purified C-reactive protein from human serum. The induction of adhesion molecules was similar to what was observed with a 24-hour incubation with interleukin-1 10 ng/mL, a well known activator of endothelial cells (FIG. 1). Although no increase in E-selectin expression was evident after 24-hour incubation with C-reactive protein (as well as with interleukin-1) (Haraldsen et al., 1996), a 6-hour incubation with C-reactive protein 10 $\mu$g/mL induced a significant increase in E-selectin (FIG. 1). A dose response for the effect of C-reactive protein on ICAM-1 and VCAM-1 expression is shown on FIG. 2. The effect was already obvious at a concentration of 5 $\mu$g/mL and was nearly maximum at 10, while increase of C-reactive protein concentration up to 200 $\mu$g/mL resulted in only a modest further adhesion molecules induction.

The inventors found that C-reactive protein, at concentration $\geq$5 $\mu$g/mL, has significant pro-inflammatory effects in endothelial cells, inducing high levels of expression of ICAM-1, VCAM-1 and E-selectin. This findings compare well with the results of previous large prospective studies, showing increased risk of cardiac events in patients with angina in the upper quintile of C-reactive protein concentrations (i.e., >3.6 $\mu$g/mL) (Haverkate et al., 1997). The highest effect is already seen at concentration of only 10 $\mu$g/mL, close to the average value in patients with refractory unstable angina (Liuzzo et al., 1994). The mechanisms of the pro-inflammatory effects of C-reactive protein on endothelial cells are not completely clear.

Example 4

Detection of Adhesion Molecules in the Absence of Serum

HUVEC were incubated with human C-reactive protein similar to Example 2 except in the absence of serum. Cells were detached by incubation with 10 mmol/L EDTA in PBS (without trypsin), washed with PBS buffer and suspended in PBS with 0.1% sodium azide. Cell were then stained with R-Phycoerythrin labeled monoclonal antibodies (Pharmingen) against the adhesion molecules VCAM-1 (CD106) or ICAM-1 (CD54) or with Phycoerythrin labeled isotype IgG as control. For detection of E-selectin, HUVEC were incubated for 6 hours with C-reactive protein and then stained with a FITC labeled monoclonal antibody against E-selectin (RandD Systems) or the appropriate isotype control (Pasceri et al., 2000). R-Phycoerythrin labeled monoclonal antibodies (Pharmingen) against the C-reactive protein receptors FC$\gamma$RI and FC$\gamma$RII (Marnell et al., 1995; Bharadwaj et al., 1999) were also used.

The staining procedure was performed on ice for 30 minutes, followed by washing. The fluorescence intensity of 9000 cells for each sample was quantified by a FACS CaliburTM analyser (Becton Dickinson). All experiments were performed in triplicate.

Figure 3A:
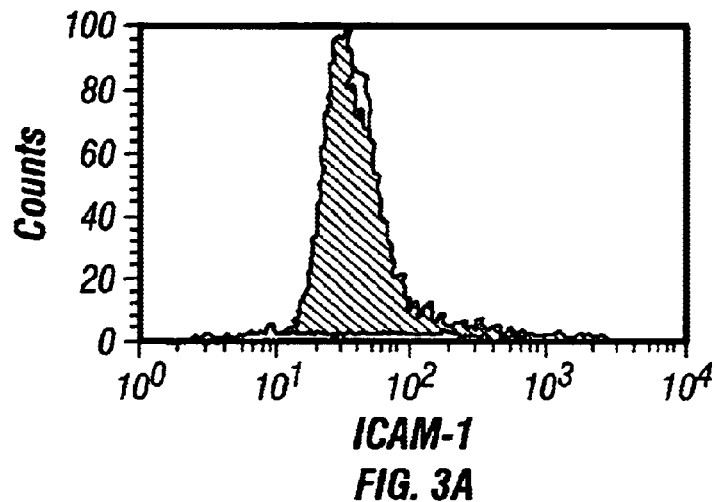
FIG. 3A, FIG. 3B and FIG. 3C: Incubation with C-reactive protein 100 $\mu$g/mL (24-hour for ICAM-1 (FIG. 3A) and VCAM-1 (FIG. 3B) and 6-hour for E-selectin (FIG. 3C)) did not induce expression of adhesion molecules in HUVEC cultured in a serum-free medium.
Figure 3B:
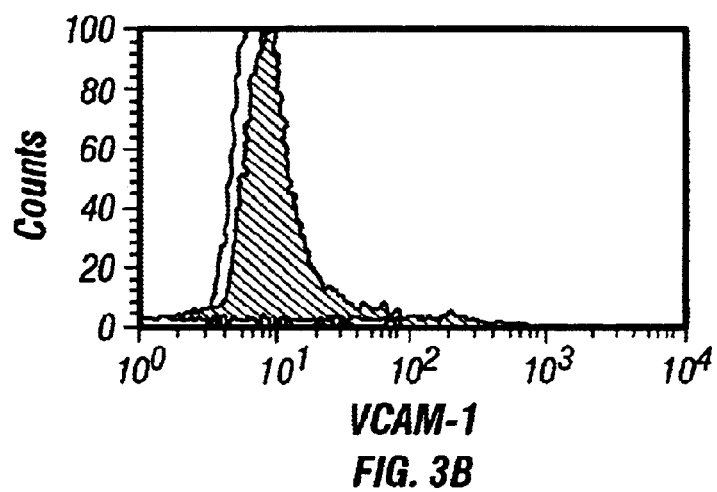
Figure 3C:
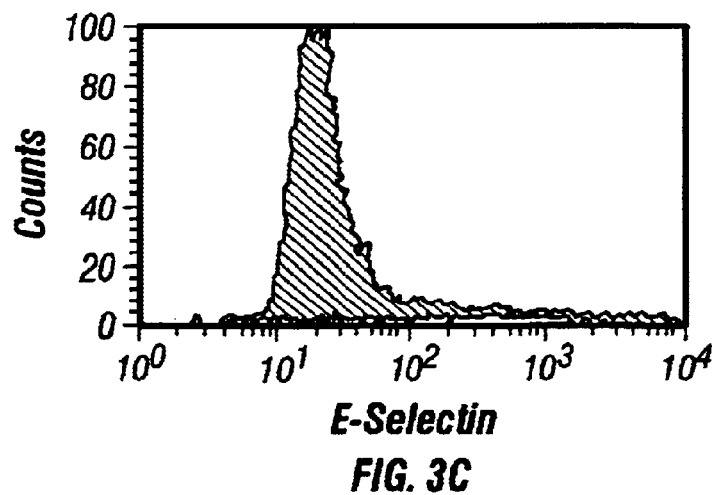

Experiments performed with HUVEC cultured in a serum-free medium showed that incubation with 100 $\mu$g/mL of C-reactive protein could not induce adhesion molecules expression (FIG. 3). This was not due to the inability of HUVEC to express adhesion molecules in the absence of serum because interleukin-1 was able to induce adhesion molecules under the same condition.

Thus, these results clearly show that the effects of C-reactive protein are dependent on the presence of serum. These results also suggest that C-reactive protein effects are dependent on one or more serum co-factors. However, this mechanism does not appear to be species-specific, since similar results have been obtained with human and bovine serum. The requirement for serum in the C-reactive protein response can also be fulfilled with bovine or guinea pig sera, suggesting that the serum factor(s) is also present in other species.

Example 5

Detection of Chemokines in the Presence of Serum

Experiments were performed in HUVEC, cultured in 12-well plates in basic endothelial cell medium CS-C, with 10 mM HEPES and 15% human serum (Sigma). Culture supernatants were collected 6–24 hours after stimulation with either IL-1β or CRP, at the concentration indicated. Secretion of MCP-1 and RANTES were assessed by sandwich ELISA (Colorimetric Quantikine, by R and D Systems). All determinations were performed in duplicate. Data were expressed as mean±SD of 5–6 separate experiments. Cell viability was assessed by staining with trypan blue.

Figure 4A:
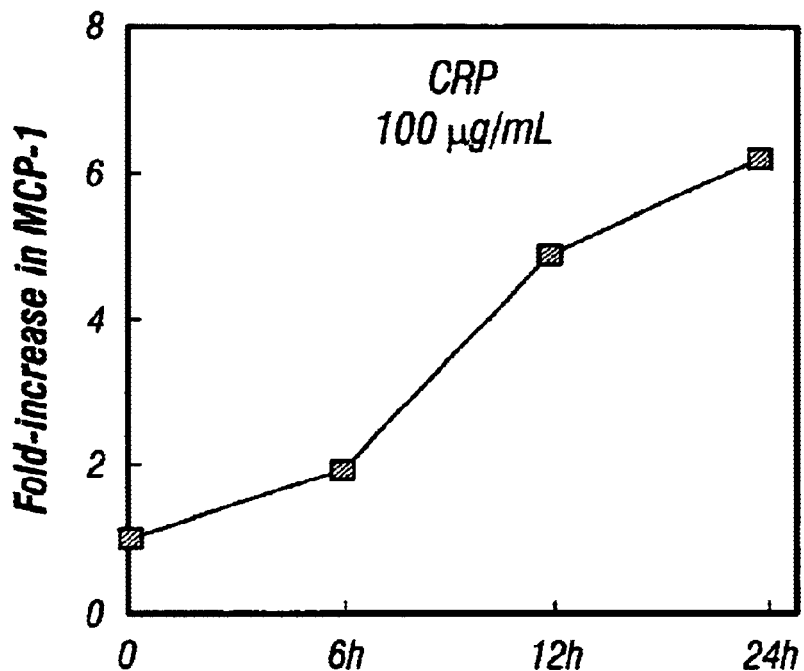
FIG. 4A, FIG. 4B and FIG. 4C: Effects of C-reactive protein on production of MCP-1 and RANTES in endothelial cells (HUVEC).

In a 24 hour time course study shown in FIG. 4A, CRP at the concentration of 100 μg/mL induces significant secretion of MCP-1, with maximal effect at 24 hours (a 7 fold-increase at 24-hour, P=0.001). Dose-response experiments, performed with 24-hour incubation, showed a significant induction of MCP-1 already with 5 μg/mL (from 1.1±0.5 ng/mL at baseline to 2.4±0.9 with 10 μg/mL of CRP) and peaked at 100 μg/mL (up to 9.7±4.8 ng/mL, P=0.001) (FIG. 4C). The maximal effects of C-reactive protein were similar to those observed after incubation with Interleukin-1β 10 ng/mL (8.6±3.7 ng/mL, FIG. 4B). Incubation with CRP 100 μg/mL for 24-hour did not induce a significant increase of MCP-1 concentrations in HUVEC in a serum-free medium (FIG. 4C), although absence of serum did not change the response to IL-1β.

Figure 4B:
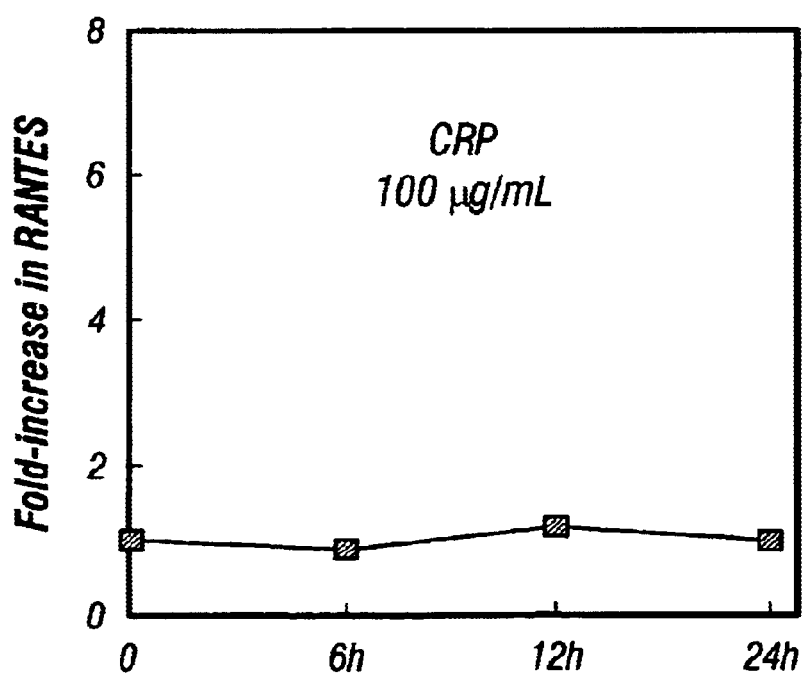
Figure 4C:
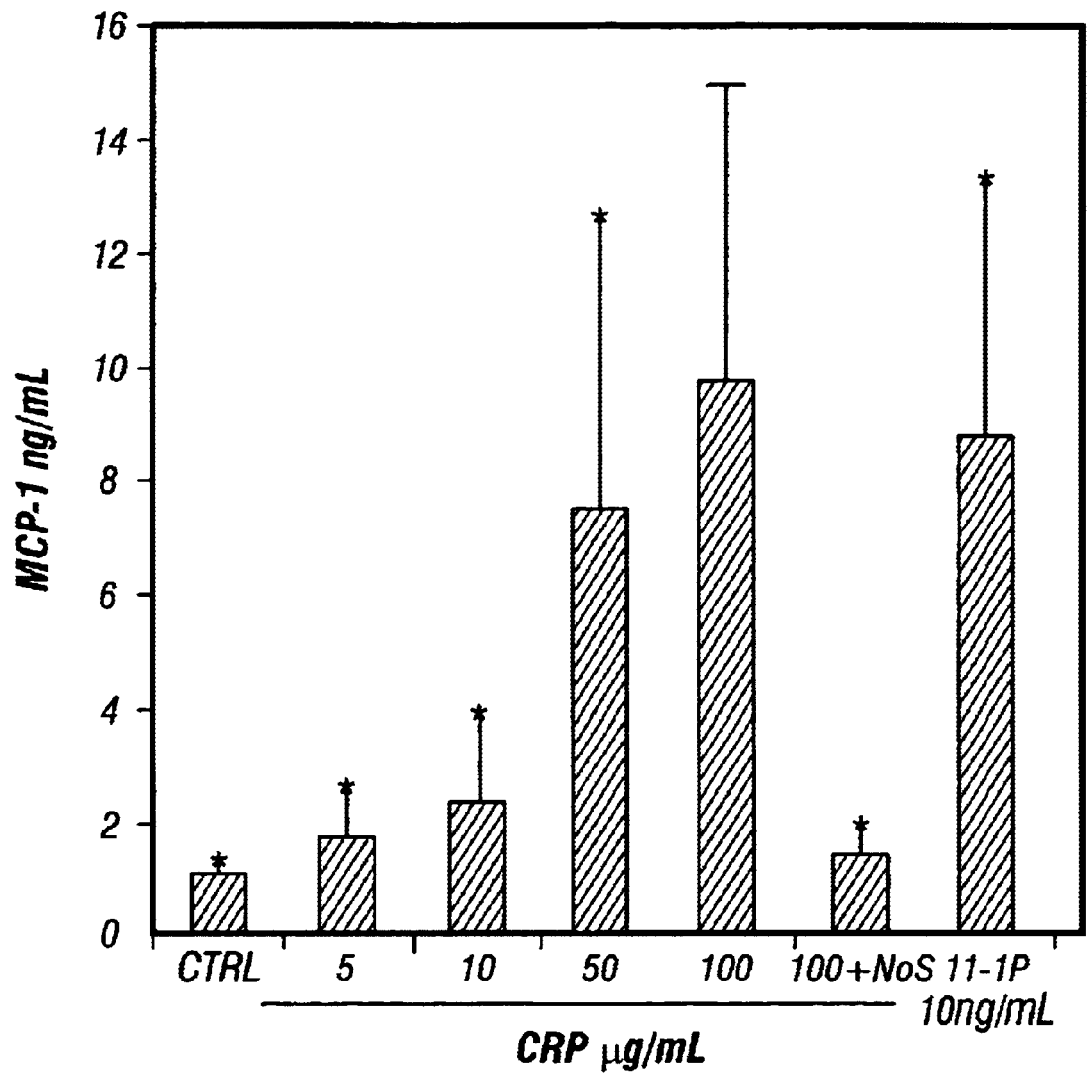

Secretion of RANTES was not increased by incubation with C-reactive protein 100 μg/mL (FIG. 4B). Similarly, incubation with Interleukin-1β 10 ng/mL did not induce RANTES expression.

Example 6

Modulation of CRP Effects by Statin and PPAR Activators

Experiments were performed in HUVEC. The cells were cultured in 12-well plates in basic endothelial cell medium CS-C, with 10 mM HEPES and 15% human serum (Sigma). The cells were also pretreated with the PPARγ agonists, troglitazone (Parke-Davis), ciglitazone (Biomol), 15-deoxy-$\Delta^{12,14}$-prostaglandin J2 (15d-PGJ2, from Calbiochem), with the PPARα agonists, fenofibrate and Wy 14649 (Sigma), or with the HMG-CoA antagonist, simvastatin, or with vehicle (0.1% DMSO or PBS) at the concentrations indicated. After 2 hours, the cells were incubated with C-reactive protein or with IL-1β 10 ng/mL for 24 hours. Simvastatin prodrug (Merck, West Point, Pa.) was activated as described (Kita et al., 1980). Secretion of MCP-1 and RANTES were assessed by sandwich ELISA (Colorimetric Quantikine, by R and D Systems). All determinations were performed in duplicate. Data were expressed as mean±SD of 5–6 separate experiments. Cell viability was assessed by staining with trypan blue.

Effects of pretreatment with simvastatin and several PPAR activators on the induction of MCP-1 are shown in the Table 1. Simvastatin 5 μM significantly reduced (about 43% of maximal response) the secretion of MCP-1 induced by CRP. Aspirin, even at high concentration (up to 1 mM) did not inhibit the effects of C-reactive protein. The PPARγ activators, troglitazone and ciglitazone, had no significant effects at low concentrations, with significant inhibition of MCP-1 secretion only at high concentration (200 μM Ciglitazone). However, 15d-PGJ2 10 μM almost completely abolished the induction of MCP-1 by CRP. PPARα activators, fenofibrate (100 μM) and Wy 14649 (100 μM), completely inhibited the secretion of MCP-1, although lower concentration (10 μM) of Wy 14649 had no effect.

TABLE 1

Effects of Simvastatin, Aspirin, and PPAR Activators on MCP-1 Induction by CRP

|  | MCP-1 conc., ng/mL | -Fold Increase in MCP-1 conc. | % of Maximal Response |
|---|---|---|---|
| Control | 2.1 ± 0.5* | 1* | 16 |
| CRP 100 μg/mL | 13.6 ± 5.4 | 6.3 ± 1.8 | 100 |
| CRP 100 μg/mL + simvastatin 4 μmol/L | 6.0 ± 2.8* | 2.7 ± 1.0* | 43 |
| CRP 100 μg/mL + aspirin 100 μmol/L | 14.6 ± 6.7 | 6.7 ± 1.9 | 104 |
| CRP 100 μg/mL + aspirin 1 mmol/L | 13.7 ± 6.7 | 6.4 ± 1.8 | 102 |
| CRP 100 μg/mL + troglitazone 20 μmol/L | 11.4 ± 5.2 | 5.2 ± 1.7 | 83 |
| CRP 100 μg/mL + ciglitazone 50 μmol/L | 10.2 ± 4.6 | 4.8 ± 1.5 | 74 |
| CRP 100 μg/mL + ciglitazone 100 μmol/L | 8.7 ± 3.4 | 4.1 ± 1.0 | 65 |
| CRP 100 μg/mL + ciglitazone 200 μmol/L | 5.9 ± 2.5* | 2.7 ± 0.8* | 42 |
| CRP 100 μg/mL + 15d-PGJ2 10 μmol/L | 3.4 ± 1.6* | 1.5 ± 0.6* | 24 |
| CRP 100 μg/mL + fenofibrate 100 μmol/L | 2.1 ± 0.6 | 0.9 ± 0.2* | 15 |
| CRP 100 μg/mL + Wy 14649 10 μmol/L | 13.9 ± 6.0 | 6.4 ± 2.1 | 101 |
| CRP 100 μg/mL + Wy 14649 100 μmol/L | 4.2 ± 2.2* | 1.9 ± 0.9* | 30 |

Values are mean ± SD or percentage.
*p < 0.05 vs. CRP 100 μg/mL alone. Values are mean ± SD or percentage.
*p < 0.05 vs. CRP 100 μg/mL alone.

Example 7

Prophylactic Administration

The modulators can be administered to a subject at risk of or suffering from inflammation in a pharmaceutical composition in an effective amount to achieve the desired result.

Modulators are administered to a subject with unstable angina or acute myocardial infarction. The route of administration is determined based upon the disease or condition to achieve the desired results. Those of skill in the art will be able to take the teachings of this specification and formulate appropriate clinical trial and treatment protocol strategies.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to the compositions and methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference.

U.S. Pat. No. 5,221,605
U.S. Pat. No. 5,238,808
U.S. Pat. No. 5,380,721
U.S. Pat. No. 5,798,208
U.S. Pat. No. 5,830,650
U.S. Pat. No. 5,220,007
U.S. Pat. No. 5,284,760
U.S. Pat. No. 5,354,670
U.S. Pat. No. 5,366,878
U.S. Pat. No. 5,389,514
U.S. Pat. No. 5,635,377
U.S. Pat. No. 5,789,166
U.S. Pat. No. 5,527,695
U.S. Pat. No. 5,658,772
Ausubel et al., In: Current Protocols in Molecular Biology, John, Wiley & Sons, Inc., 1994.
Bharadwaj D, et al., *J Exp Med* 1999; 190:585–90.
Biasucci L M, et al., *Circulation* 1999; 99:855–860.
Cermak J, et al., *Blood* 1993; 82:513–20.
Ferreiros E R, et al., *Circulation* 1999; 100:1958–63.
Haraldsen G, et al., *J Immunol* 1996; 156:2558–65.
Haverkate F, et al., *Lancet* 1997; 349:462–6.
Kilpatrick J M and Volanakis J E. *Immunol Res* 1991; 10:43–53.
Kita T, et al., *J Clin Invest* 1980; 66:1094–100.
Koenig W, et al., *Circulation* 1999; 99:237–42.
Lagrand W K, et al., *Circulation* 1999; 100:96–102.
Libby P, et al., *Ann N Y Acad Sci* 1997; 811:134–42; discussion 142–5.
Liuzzo G, et al., *N Engl J Med* 1994; 331:417–24.
Marnell L L, et al., *J Immunol* 1995; 155:2185–93.
Maseri A. *N Engl J Med* 1997; 336:1014–6.
Pasceri V, et al., *Circulation* 2000; 101:235–8.
Pasceri V and Yeh E T. *Circulation* 1999; 100:2124–6.
Reynolds G D and Vance R P. *Arch Pathol Lab Med* 1987; 111:265–9.
Ridker P M, et al., [published erratum appears in *N Engl J Med* Jul. 31, 1997; 337(5):356]. *N Engl J Med* 1997; 336:973–9.
Ridker P M, et al., *N Engl J Med* 2000; 342:836–43.
Ridker P M, et al, *Circulation* 1999; 100:230–5.
Sambrook, Fritsch, Maniatis, *Molecular Cloning: A Laboratory Manual,* 2nd Ed., Cold Spring Harbor Press, Cold Spring Harbor, N.Y., 1989.
Shah P K. *Circulation* 2000; 101: 1758–9.
Torzewski J, et al., *Arterioscler Thromb Vasc Biol* 1998; 18:1386–92.

What is claimed is:

1. An in vitro method of screening for modulators of human C-reactive protein in serum comprising:

obtaining a human C-reactive protein from human serum;

contacting the C-reactive protein with at least a first candidate substance in vitro;

assaying for an interaction between the C-reactive protein and the candidate substance by assaying for C-reactive protein induction of the expression of ICAM-1, VCAM, or E-selectin in endothelial cells wherein the induction expression of ICAM-1, VCAM, or E-selectin is an indication that the candidate substance is a modulator.

2. The method of claim 1, wherein the identity of the first candidate substance is unknown prior to performance of the screening method.

3. The method of claim 1, wherein the first candidate substance is comprised in a mixture of possible candidate substances.

4. The method of claim 1, further comprising determining the identity of the first candidate substance after the performance of the screening method.

5. The method of claim 1, further comprising isolating the first candidate substance after the performance of the screening method.

6. The method of claim 1, further comprising determining characteristics of the first candidate substance after the performance of the screening method.

* * * * *